United States Patent [19]

Zirngibl et al.

[11] Patent Number: 4,554,356

[45] Date of Patent: Nov. 19, 1985

[54] METHOD FOR PRODUCTION OF IMIDAZOLYL VINYL ETHERS

[75] Inventors: Ludwig Zirngibl; Kurt Thiele, both of Zofingen, Switzerland

[73] Assignee: Siegfried Aktiengesellschaft, Zofingen, Switzerland

[21] Appl. No.: 692,324

[22] PCT Filed: Jan. 21, 1982

[86] PCT No.: PCT/EP82/00010

§ 371 Date: May 24, 1982

§ 102(e) Date: May 24, 1982

[87] PCT Pub. No.: WO82/02552

PCT Pub. Date: Aug. 5, 1982

Related U.S. Application Data

[63] Continuation of Ser. No. 566,776, Dec. 29, 1983, abandoned, which is a continuation of Ser. No. 385,403, May 24, 1982, abandoned.

[30] Foreign Application Priority Data

Jan. 23, 1981 [CH] Switzerland ............................ 430/81

[51] Int. Cl.[4] ............................................. C07D 233/60
[52] U.S. Cl. .................................... 548/341; 546/278; 548/336; 548/337; 548/338
[58] Field of Search ................ 548/341, 336, 337, 338; 546/278

[56] References Cited

U.S. PATENT DOCUMENTS 4,210,657  7/1980  Zirngibl et al. .................. 548/336 X

OTHER PUBLICATIONS

House, H., *Modern Synthetic Reactions*, 2nd Ed., Benjamin/Cummings, Menlo Park, CA, 1972, pp. 520–530.

Dehmlow, E. et al., *Phase Transfer Catalysis*, Verlag Chemie, Deerfield Beach, FL, 1980, pp. 120–133.

*Primary Examiner*—Richard A. Schwartz
*Attorney, Agent, or Firm*—Jordan and Hamburg

[57] ABSTRACT

A process for the manufacture of imidazolylvinyl ethers of the formula

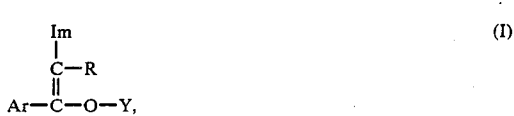

wherein Im represents the substituted or unsubstituted 1-H-imidazol-1-yl group and An, R and Y are defined hereinbelow by condensation of a corresponding ketone of the formula

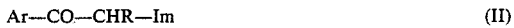

with the splitting-off of a Z group, with a condensable substance of the formula

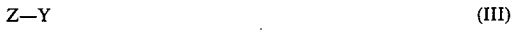

in the aqueous solution of a strong inorganic base, preferably in concentrated aqueous soda lye. The reaction may also be carried out in the presence of a second liquid organic phase, preferably benzene or toluene, especially in the presence of a phase transfer catalyst in this case. Through careful crystallization of the product manufactured according to this method, it is possible to manufacture approximately pure E-isomers of the imidazolylvinyl ether of formula (I), without the requirement of chromatographic separation.

17 Claims, No Drawings

METHOD FOR PRODUCTION OF IMIDAZOLYL VINYL ETHERS

This application is a continuation of application Ser. No. 566,776, filed Dec. 29, 1983, said Ser. No. 566,776 being a continuation of U.S. Ser. No. 385,403, filed May 24, 1982, now abandoned.

BACKGROUND OF THE INVENTION AND PRIOR ART STATEMENT

This invention relates to a process for the manufacture of imidazolylvinyl ethers of the formula

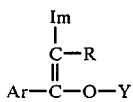   (I)

and their acid addition salts, wherein in formula (I)
Ar represents phenyl, naphthyl, thienyl or pyridyl, wherein these rings may be mono- or multi-substituted, and the substituents, independently from each other, may represent a halogen, a lower alkyl or a cycloalkyl with up to 6 carbon atoms, trifluoromethyl, a lower alkoxy or lower alkylthio with 1 to 6 carbon atoms in the alkyl portion in each case, phenyl, benzyl, cyano, nitro or amino,
R represents hydrogen, an unbranched or branched alkyl with up to 6 carbon atoms, phenyl or a phenyl-substituted alkyl with up to 6 carbon atoms in the alkyl portion, wherein the phenyl may be substituted by halogen, alkyl or alkoxy with up to 6 carbon atoms in the alkyl portion in each case,
Im represents the 1-H-imidazol-1-yl group, which may be monosubstituted by the nitro group or mono-, di- or tri-substituted by halogen or an alkyl or alkoxy group with 1 to 4 alkyl carbon atoms, and
Y represents an unbranched, branched or cyclic, saturated or one double bond containing unsaturated alkyl with up to 6 carbon atoms, phenyl, naphthyl, thienyl or pyridyl or an alkyl substituted with phenyl, naphthyl, pyridyl or thienyl having 1 to 6 carbon atoms in the alkyl portion, wherein all the preceding groups, including the alkyl groups, may in each case be substituted as stated above for the Ar group, and wherein any alkyl group bonded directly to the ether oxygen or any alkylene group bonded directly to the ether oxygen may contain the bivalent groups —O—, —S—, —SO—, or —SO$_2$— once or twice in the chain, or may terminally carry one of these groups in the ω-position in relation to the ether oxygen, wherein this group is then saturated with one of the groups mentioned above for Ar, through the reaction of a corresponding ketone of the formula

in which Ar, R and Im have the aforementioned meanings in an alkaline medium with a compound of the formula

in which Z is an alkaline splittable group, and separation of the reaction product.

In formula (I), if the group is Ar, the groups will be phenyl, naphthyl, thienyl or pyridyl, preferably particularly mono- or di-substituted, preferably by a halogen, especially chlorine or bromine, as well as an unbranched or branched acyclic alkyl with 1 to 4 carbon atoms, especially methyl or ethyl. In the single-member ring system that may represent Ar, the substituents possibly present are preferably in the 2 and/or 4 position.

The R group in formula (I) is preferably hydrogen or an unbranched or branched acyclic alkyl with 1 to 4 carbon atoms, especially methyl or ethyl.

The Im group in formula (I) is preferably particularly an unsubstituted 1-H-imidazol-1-yl group or is the same group mono-, di, or tri- but preferably, mono-substituted by a halogen, especially chlorine or bromine, and/or methyl.

Finally, group Y in formula (I) is preferably an unbranched or branched acyclic unsaturated alkyl group with 1 or 6 carbon atoms, a lower alkoxy-lower alkyl group, a phenyl-lower alkoxy-lower alkyl group, a phenoxy-lower alkyl group, a phenoxy-lower alkoxy-lower alkyl group or a lower alkyl-amino-lower alkyl group, wherein "lower alkyl" and "lower alkoxy" in all preceding cases are to be understood as groups with 1 to 4 carbon atoms and the phenyl group may be mono-, di-, or tri-substituted, especially mono- or di- by halogen, especially chlorine or bromine, in the 4 and/or 2 position.

In formula (III), the alkaline splittable group is, for instance, a halogen atom, especially a chlorine or bromine atom, or also an organic acid group, for example toluene sulfone acid.

This invention further relates to the utilization of the process of the invention.

The aforementioned process for the manufacture of imidazolylvinyl ethers of formula (I) is known from publication EP No. 8 804 A1 as well as, with small variations, from publications DE No. 27 57 113 A1 and DE No. 28 39 388 A1. According to this known method, condensation of the ketone obtained as a 1-arylcarbonylalkylimidazole of formula (II) is carried out with a group Z containing a substance of formula (III), splittable through condensation in the presence of a base, especially sodium hydride, in a polar aprotic solvent, especially in hexamethylphosphoric acid triamine or in dimethylformamide. Alkali metals, alkaline earth metals, their hydrides and alchoholates, organic lithium compounds, and unsubstituted or N-substituted sodium amide may be used as condensation agents besides the mentioned sodium hydride.

The condensation agents and aprotic solvents required to carry out the known process are expensive substances. In addition, their use may trigger toxicological and ecological side effects. Finally, the known condensation reaction leads to an isomeric mixture in which the E-isomers as well as the Z-isomers of the imidazolylvinyl ether of formula (I) is present in approximately equal parts. Considering that the E-isomers in almost all cases are the most active isomers concerning their bactericide and fungicidal qualities and the product obtained as an isomeric mixture for this reason has to be chromatographically separated, the known process is also only moderately suitable from an economical point of view for the production of larger amounts of products. Another drawback is that, frequently, instead of the O-alkylation intended by condensation, a C-alkylation also occurs so that, for this reason, the reaction product obtained by the known process requires additional separation by column chromatography. This is not economical from the vantage point of industrial production of the imidazolylvinyl ether of formula (I).

SUMMARY OF THE INVENTION

This invention has the object of making the aforedescribed known process for the production of imidazolylvinyl ethers of formula (I) more economical, to apply reaction systems that on use have lower toxicological and ecological side effects and to make production of E-isomers easier and more economical.

To accomplish this object, the aforedescribed known method is transformed in a distinctive manner so that conversion no longer occurs in an aprotic solvent, but in the aqueous solution of a strong inorganic base, thus in a typical protic reaction system.

The bases used in this process to carry out the condensation reaction are, above all, substantially less expensive than the polar aprotic solvents required by the prior art and the required expensive condensation agents, for instance the sodium hydride dispersed in an oil used in the prior art. In addition, the aqueous, inorganic bases used in the process of this invention also exhibit less toxicological and ecological side effects, the equipment involved also being more economical than the known reaction systems used up to now.

Finally, it is to be noted that on using the process of this invention, as the reaction is carried out in the aqueous solution of a strongly inorganic base, the imidazolylvinyl ethers of formula (I) are obtained in the form of isomeric mixtures that for the most part comprise E-isomers. From such product mixtures, almost pure E-isomers can be obtained through simple crystallization. Chromatographic separation of the isomeric mixtures may be omitted in most cases. The stereochemical purity achievable herein through simple crystallation of the E-isomers almost always suffices to make the crystallized product available for therapeutic uses.

Concentrated aqueous soda lye is preferably employed as the aqueous solution of a strong inorganic base, especially at least a two-normal aqueous soda lye.

DETAILED DESCRIPTION OF PREFERRED EMBODIMENTS

In one embodiment of the present invention, the condensation reaction between the substances of formulas (II) and (III) is preferably carried out in the presence of a second liquid, namely an organic phase in the reaction system. For this reason, a liquid apolar hydrocarbon in particular, preferably benzol or toluol, is added to the liquid reaction system. To improve phase separation, the reaction is preferably carried out in the presence of a phase transfer catalyst.

Quaternary ammonium or phosphonium salts have been known to be suitable as phase transfer catalysts. Examples of such salts have been compiled in the monograph by W. P. Weber and G. W. Gockel, Phase Catalysis in Organic Synthesis, Berlin, Springer Verlag, 1977. Tertabutylammonium hydroxide, and also triethylbenzylammonium chloride and benzyl-dimethyl-tetradecylammonium bromide, have been found to be especially suited for such purposes.

The working up and separation of the reaction product is carried out in the known, conventional manner through distillation, filtration or precipitation, especially through precipitation with acids which, together with the imidazolylvinyl ethers of formula (I), form acid addition salts. Precipitation is preferably effected with concentrated nitric acid.

The almost sterically pure E-isomers of the imidazolyl vinyl ethers of formula (I) can be obtained by carefully allowing the products, especially the salts, to crystallize.

The invention is explained in more detail by way of example of embodiments.

EXAMPLE 1

2-(2,4-dichlorophenyl)-2-methoxy-1-(imidazol-1-yl)-ethylene nitrate

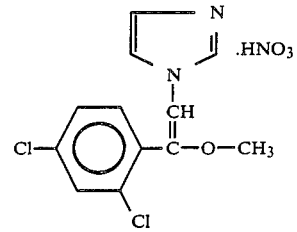

A mixture of 58.32 g (0.2 mol) 1-(2,4-dichlorophenacyl)-imidazole and 200 ml of 2n NaOH is mixed, drop by drop, at room temperature, under stirring, with 37.25 g (0.2 mol) p-toluene sulfonic acid methyl ester. Next, the reaction mixture is stirred 3 days at room temperature. The reaction mixture thereafter is initially shaken with ether and then with chloroform. The extracts are dried with sodium sulfate and then combined and evaporated. The oil remaining as residue is dissolved in dichloromethane and chromatographed in a column filled with 500 g silica gel. Uniformity of the elution fractions is checked by thin-layer-chromatography. The uniform fractions are combined. The solvent is distilled from the combined fractions. The remaining oily residue is dissolved in ether. From this solution, the end product is precipitated with 65% nitric acid in the form of nitrate. The crystals are separated through filtration and re-crystallized from ethyl acetate. The purified end product has a melting point between 152° and 153° C. Uniformity, purity and identity of the thus obtained nitrate are ensured through elementary analysis and through the IR-spectrum.

EXAMPLE 2

2-(2,4-dichlorophenyl)-2-(2-(4-chlorophenoxy)-ethoxy)-1-(imidazol-1-yl)-ethylene nitrate

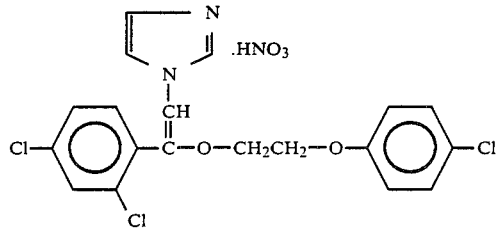

A mixture of 291.6 g (1 mol) 1-(2,4-dichlorophenacyl)-imidazole, 800 ml of 50% aqueous soda lye, 80 ml of a 40% aqueous tetrabutylammonium hydroxide solution and 800 ml toluene are heated at 50° C. 353.3 g (1.5 mol) 1-bromo-2-(4-chlorophenoxy)-ethane, dissolved in 200 ml toluene, is instilled under vigorous stirring at this temperature, in the course of 3 hours. The two liquid phases are separated after cooling. The organic phase is washed twice with water, dried over sodium sulfate and evaporated under reduced pressure. The residue is a dark oil which is dissolved in 850 ml ethyl acetate. The solution is then mixed with 100 ml of 65% aqueous nitric acid. The nitric acid solution is then cooled and mixed portion-wise with a total of 500 ml ether. The nitrate product precipitates herein. The precipitate is separated on a suction filter and subsequently washed with ethyl acetate and ether. The still highly yellowish colored crystals are re-crystallized from ethyl acetate. The purified and practically colorless end product, which is obtained in a yield of 42% of the theoretical yield, has a melting point between 145° and 147° C.

Purity and identity of the obtained nitrate product are ensured through elementary analysis and IR-spectrum.

EXAMPLE 3

E-1-(2,4-dichlorophenyl)-1-(2-(4-chlorophenoxy)-ethoxy)-2-(imidazol-1-yl)-propene nitrate

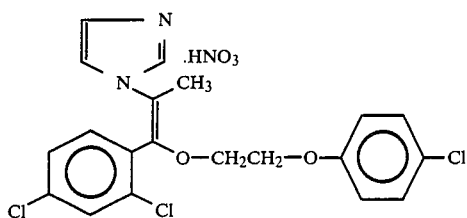

166. g (0.5 mol) 1-(2,4-dichlorophenyl)-2-(imidazol-1-yl)propan-1-one, 400 ml of a 50% aqueous soda lye, 400 ml benzene and 40 ml of a 40% aqueous solotion of tetrabutyl ammonium hydroxide are mixed and heated to 50° C. under vigorous stirring. 141 g 1-bromo-2-(4-chlorophenoxy)-ethane, dissolved in 400 ml benzene, is instilled into the stirred and warmed solution in the course of 10 hours. The mixture is subsequently stirred for another 15 hours at 50° C. Then, with analytical control, in this case with thin-layer chromatography, stirring is continued at room temperature until the reaction is completed, in this case another 24 hours. After completion of the reaction, the reaction mixture is mixed with as much water and chloroform so that the aqueous phase becomes lighter than the organic phase. Thereafter, the organic and aqueous phases are separated. The organic phase is dried with sodium sulfate. The solvents are distilled under reduced pressure. The remaining residue is a dark oil that is dissolved in about 500 ml ethyl acetate. The solution is diluted with 250 ml ether and then adjusted to a pH-value of 5 by means of 65% aqueous nitric acid. The thus derived nitric acid solution is then cooled in the refrigerator. The impure precipitated product herein is subsequently re-crystallized from a mixture of 250 ml ethyl acetate and 250 ml ethanol. The purified product has a melting point of 121° C., and may be analytically identified as an approximately pure E-isomer of propylene nitrate.

EXAMPLE 4

2-(2,4-dichlorophenyl)-2-butoxyethoxy-1-(imidazol-1-yl)ethylene nitrate

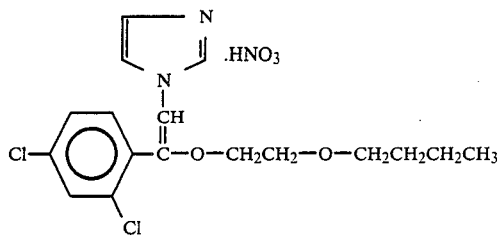

The method described in Example 2 is repeated with the change that, instead of 1-bromo-2-(4-chlorophenoxy)-ethane, the equimolar amount of 1-bromo-2-n-butoxy-ethane is used. After re-crystallization, the purified nitrate has a melting point between 191° and 192° C.

EXAMPLE 5

1-(2,4-dichlorophenyl)-1-(2,4-dichlorophenoxyethoxy)-2-(imidazol-1-yl)propane nitrate

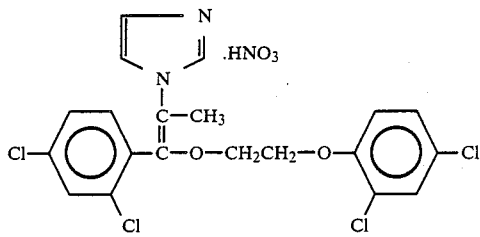

The method described in Example 3 is repeated with the change that, instead of 1-bromo-2-(4-chlorophenoxy)-ethane, the equimolar amount of 1-bromo-2-(2,4-dichlorophenoxy)-ethane is used. The purified end product, which comprises the E-isomer almost exclusively, has a melting point between 118° and 120° C.

EXAMPLE 6

2-(2,4-dichlorophenyl)-2-(4-chlorobenzyloxy)-1-(imidazol-1-yl)ethylene nitrate

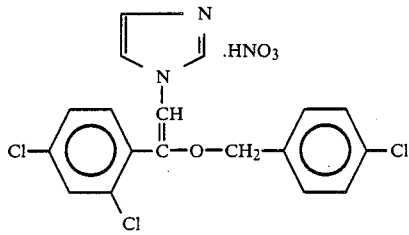

The example described in Example 2 is repeated with the change that, instead of 1-bromo-2-(4-phenoxy)-ethane, the equimolar amount of p-bromomethylchlorobenzene is used.

The recrystallized end product has a melting point between 117° and 118° C.

EXAMPLE 7

2-(2,4-dichlorophenyl)-2-(4-chlorobenzyloxy)-ethoxy)-1-(imidazol-1-yl)-ethylene nitrate

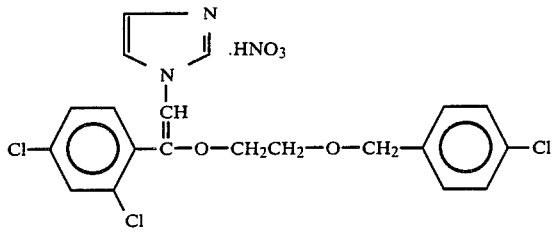

The method described in Example 2 is repeated with the change that, instead of 1-bromo-2-(4-phenoxy)-ethane, the equimolar amount of 1-bromo-2-(4-chlorobenzyloxy)-ethane is used.

The recrystallized end product, which has a surprisingly high biocidal activity, has a melting point between 119° and 121° C.

We claim:

1. Process for the production of an imidazolyl-vinyl ether of the formula

or an acid addition salt thereof, wherein in formula (I)

Ar represents a phenyl, napthyl, thienyl or pyridyl ring, wherein said ring optionally is mono- or multi-substituted and the substituents, independently from each other, represent a halogen, a lower alkyl group or a cycloalkyl group with up to 6 carbon atoms, a trifluoromethyl, a lower alkoxy or a lower alkylthio group with 1 to 6 carbon atoms in the alkyl portion thereof, a phenyl, benzyl, cyano, nitro, amino or loweralkyl amino group, R represents hydrogen, an unbranched or branched alkyl group with up to 6 carbon atoms, phenyl, or a phenyl-substituted alkyl group with up to 6 carbon atoms in the alkyl portion, wherein said phenyl group optionally is substituted by halogen, alkyl or alkoxy with up to 6 carbon atoms in the alkyl portion thereof, Im represents the 1-H-imidazol-1-yl group, which may be mono-substituted by the nitro group or mono-, di- or tri-substituted by halogen or an alkyl or alkoxy group with 1 to 4 alkyl carbon atoms, and Y represents an unbranched, branched or cyclic, saturated or doble bond containing unsaturated alkyl with up to 6 carbon atoms, phenyl, naphthyl, thienyl or pyridyl or an alkyl substituted with a phenyl, naphthyl, pyridyl or thienyl group having 1 to 6 carbon atoms in the alkyl portion, wherein all the preceding groups, including the alkyl groups, may, in each case, be substituted as stated above for the Ar group, and wherein any alkyl group directly bonded to the ether oxygen or any alkylene group bonded directly to the ether oxygen may contain the bivalent groups —O—, —S—, —SO—, or —SO$_2$— once or twice in the chain, or may terminally carry one of these groups in the ω-position in relation to the ether oxygen, said group being then saturated with one of the groups mentioned for Ar, through the reaction of a corresponding ketone of the formula $$Ar—CO—CHR—Im \quad (II),$$

in which Ar, R and Im have the aforementioned meanings, in an alkaline medium with a compound of the formula $$Z—Y \quad (III),$$

in which Y is as above-defined, Z is an alkaline splittable group and separation of the reaction product, wherein said reaction is carried out in an aqueous solution of a strong inorganic base.

2. The process of claim 1 wherein

Ar is mono- or multi-substituted with chlorine or bromine, or an unbranched or branched acyclic alkyl of one to four carbon atoms, in the 2 and/or 4 position of a single-ring Ar, R is hydrogen or an unbranched or branched acyclic alkyl of 1 to 4 carbon atoms, Im is an unsubstituted 1-H-imidazol-1-yl group or is mono-, di-, or tri-substituted with any combination of halogen and/or methyl, Y is an unbranched or branched acyclic unsaturated alkyl group of one to six carbon atoms, a lower alkoxy-lower alkyl group, a phenyl-lower alkoxy-lower alkyl group, a phenoxy-lower alkyl group, a phenoxy-lower alkoxy-lower alkyl group, or a lower alkyl-amino-lower alkyl group, wherein the phenyl portion of these groups is unsubstituted or mono-, or di-substituted by halogen in the 4 and/or 2 position, and Z is halogen or an organic acid group.

3. A process according to claim 2, characterized in that the reaction is carried out in the presence of a second liquid organic phase.

4. A process according to claim 3, characterized in that reaction in the two-phase system is carried out in the presence of a phase-transfer catalyst.

5. A process according to claim 4, characterized in that a concentrated aqueous soda lye will serve as the aqueous solution of a strongly inorganic base.

6. A process according to claim 3, characterized in that either benzene or toluene is employed as the second phase.

7. A process according to claim 4, characterized in that the phase transfer catalyst is tetrabutyl ammonium hydroxide.

8. The process of claim 5 wherein the phase transfer catalyst is quaternary ammonium and/or phosphonium salts.

9. The process of claim 7 wherein precipitation is carried out with nitric acid.

10. Process according to claim 9 for the manufacture of E-isomers of formula (I) through crystallization of the reaction product obtained.

11. The process of claim 2 for forming 2-(2,4-dichlorophenyl)-2-methoxy-1-(imidazol-1-yl)-ethylene nitrate by reacting 1-(2,4-dichlorophenacyl)-imidazole and p-toluene sulfonic acid methyl ester in sodium hydroxide, followed by precipitation with nitric acid.

12. The process of claim 7 for forming 2-(2,4-dichlorophenyl)-2-(2-(4-chlorophenoxy)-ethoxy)-1-(imidazol-1-yl)-ethylene nitrate by reacting 1-(2,4- dichlorophenacyl)-imidazole and 1-bromo-2-(4-chlorophenoxy)-ethane in the presence of aqueous soda lye, tetrabutyl ammonium hydroxide, and toluene, followed by phase separation and precipitation with nitric acid.

13. The process of claim 10 for forming E-1-(2,4-dichlorophenyl)-1-(2-(4-chlorophenoxy)-ethoxy)-2-(imidazol-1-yl)-propene nitrate by reacting 1-(2,4-dichlorophenyl)-2-(imidazol-1-yl)propan-1-one and 1-bromo-2-(4-chlorophenoxy)ethane in the presence of aqueous soda lye, benzene, and tetrabutylammonium hydroxide, followed by phase separation, precipitation with nitric acid, and recrystallization.

14. The process of claim 7 for forming 2-(2,4-dichlorophenyl)-2-butoxyethoxy-1-(imidazol-1-yl)-ethylene nitrate by reacting 1-(2,4-dichlorophenacyl)-imidazole and 1-bromo-2-n-butoxy-ethane in the presence of aqueous soda lye, tetrabutyl ammonium hydroxide, and toluene, followed by phase separation and precipitation with nitric acid.

15. The process of claim 10 for forming E-1-(2,4-dichlorophenyl)-1-(2,4-dichlorophenoxy-ethoxy)-2-(imidazol-1-yl)propene nitrate by reacting 1-(2,4-dichlorophenyl)-2-(imidazol-1-yl)propan-1-one and 1-bromo-2-(2,4-dichlorophenoxy)-ethane, in the presence of aqueous soda lye, benzene, and tetrabutylammonium hydroxide, followed by phase separation, precipitation with nitric acid and recrystallization.

16. The process of claim 7 for forming 2-(2,4-dichlorophenyl)-2-(4-chlorobenzyloxy)-1-(imidazol-1-yl)-ethylene nitrate by reacting 1-(2,4-dichlorophenacyl)-imidazole and p-bromomethylchlorobenzene in the presence of aqueous soda lye, tetrabutyl ammonium hydroxide, and toluene, followed by phase separation and precipitation with nitric acid.

17. The process of claim 7 for forming 2-(2,4-dichlorophenyl)-2-(2-(4-chlorobenzyloxy)-ethoxy)-1-(imidazol-1-yl)-ethylene nitrate by reacting 1-(2,4-dichlorophenacyl)-imidazole and 1-bromo-2-(4-chlorobenzyloxy)ethane in the presence of aqueous soda lye, tetrabutyl ammonium hydroxide, and toluene followed by phase separation and precipitation with nitric acid.

* * * * *